(12) United States Patent
Jagadeesh

(10) Patent No.: US 8,513,019 B2
(45) Date of Patent: Aug. 20, 2013

(54) APPARATUS AND METHOD FOR GENETICALLY TRANSFORMING CELLS

(75) Inventor: Gopalan Jagadeesh, Bangalore (IN)

(73) Assignee: Indian Institute of Science, Bangalore (IN)

( * ) Notice: Subject to any disclaimer, the term of this patent is extended or adjusted under 35 U.S.C. 154(b) by 0 days.

(21) Appl. No.: 13/560,086

(22) Filed: Jul. 27, 2012

(65) Prior Publication Data

US 2012/0295356 A1 Nov. 22, 2012

Related U.S. Application Data

(62) Division of application No. 12/480,508, filed on Jun. 8, 2009, now Pat. No. 8,232,093.

(30) Foreign Application Priority Data

Feb. 5, 2009 (IN) .............................. 256/CHE/2009

(51) Int. Cl.
*C12N 15/00* (2006.01)

(52) U.S. Cl.
USPC ........... 435/455; 435/459; 435/468; 435/470; 435/471; 435/285.2; 435/285.3

(58) Field of Classification Search
None
See application file for complete search history.

(56) References Cited

U.S. PATENT DOCUMENTS

| | | |
|---|---|---|
| 5,080,016 A | 1/1992 | Osher |
| 5,206,455 A | 4/1993 | Williams et al. |
| 6,386,108 B1 | 5/2002 | Brooks et al. |
| 6,613,972 B2 * | 9/2003 | Cohen et al. ................... 136/209 |
| 6,767,743 B2 | 7/2004 | Takayama et al. |
| 7,055,437 B1 | 6/2006 | Robinson et al. |
| 2009/0105738 A1* | 4/2009 | Apperson et al. ............. 606/167 |

FOREIGN PATENT DOCUMENTS

| | | |
|---|---|---|
| IN | 454/CHE/2005 | 2/2006 |
| WO | WO-94/24263 | 10/1994 |

OTHER PUBLICATIONS

Jagadeesh, et al., "Shock Waves Can Enhance Bacterial Transformation with Plasmid DNA," Current Science, (2004), vol. 87, No. 6, pp. 734-735, Current Science Association.
Klein, et al., "High-Velocity Microprojectiles for Delivering Nucleic Acids into Living Cells", Nature, (May 7, 1987), vol. 327, No. 6117, pp. 70-73, Nature Publishing Group.
Kodama, et al., "Cytoplasmic Molecular Delivery with Shock Waves: Importance of Impulse", Biophysical Journal, (2000), vol. 79, No. 4, pp. 1821-1832, Cell Press.
Oommen, et al., "Studies on micro explosive driven blast wave propagation in confined domains using NONEL tubes", in *Shock Waves, 26th International Symposium on Shock Waves, Proceedings* vol. 2, Gottingen, Germany, Jul. 15-20, 2007, Eds. Hannemann, et al., Springer Verlag 2009, pp. 1515-1520 (6 pages).
Shangguan, et al., "Drug Delivery with Microsecond Laser Pulses into Gelatin," Applied Optics, (1996), vol. 35, No. 19, 3347-3357, Optical Society of America.
Shangguan, et al., "Photoacoustic Drug Delivery: The Effect of Laser Parameters on Spatial Distribution of Delivered Drug," in *SPIE Proceedings of Laser-Tissue Interaction VI*, Ed. S.L. Jacques, Proceedings of SPIE, (1995), vol. 2391, pp. 394-402.
U.S. Non-final Office Action received for U.S. Appl. No. 12/480,508 dated Oct. 25, 2011.
U.S. Notice of Allowance received for U.S. Appl. No. 12/480,508 dated Mar. 30, 2012.

\* cited by examiner

*Primary Examiner* — Jim Ketter
(74) *Attorney, Agent, or Firm* — Foley & Lardner LLP

(57) ABSTRACT

A fluid containing cells and free genetic material is acoustically coupled to a propulsion surface of a diaphragm. A blast-receiving surface of the diaphragm is acoustically coupled to an explosion chamber in which an explosive material is disposed. An ignition system ignites the explosive material in the explosion chamber to create a blast wave. The diaphragm transfers momentum from the blast wave to the fluid containing cells and free genetic material sufficient to cause the cells to take up the free genetic material.

9 Claims, 6 Drawing Sheets

APPARATUS AND METHOD FOR GENETICALLY TRANSFORMING CELLS

CROSS-REFERENCE TO RELATED APPLICATIONS

This application is a Divisional of U.S. patent application Ser. No. 12/480,508, entitled: Apparatus and method for Genetically Transforming Cells, the contents of which are incorporated by reference herein in its entirety.

This application claims priority to Indian Provisional Application No. 256/CHE/2009, filed Feb. 5, 2009, the contents of which are incorporated by reference herein in its entirety.

BACKGROUND

As scientists continue to discover the genetic causes of many diseases, the need for safe and effective gene therapy increases. Gene therapy may be a solution to major diseases such as cancer, cardiovascular disease, and inherited metabolic disorders, among other diseases and disorders. See Kodama, et al., *Cytoplasmic Molecular Delivery with Shock Waves: Importance of Impulse,* 79 BIOPHYSICAL JOURNAL 1821, 1821 (October 2000). A device that is able to safely and effectively genetically transform cells could be useful in cancer treatment, HIV treatment, and other treatments involving genetic therapies.

One conventional method of cell transformation uses an electroporator. In the electroporator method, an electrode is dipped into a solution of DNA and the cells to be transformed. However, the salt concentration of the solution and the electrode material are potential sources of contamination.

Other methods of cell transformation include the KCM method and the freeze-thaw method. In the KCM method, cells are mixed with plasmid DNA and KCM buffer (5× buffer–500 mM KCl, 150 mM $CaCl_2$, 250 mM $MgCl_2$), incubated in ice for 20 minutes, and then kept at room temperature for 10 minutes. After incubation, the cells are grown and selected. See Jagadeesh, et al., *Shock Waves Can Enhance Bacterial Transformation with Plasmid DNA,* 87 CURRENT SCIENCE 734, 734 (Sep. 25, 2004). In the freeze-thaw method, competent cells are thawed on ice, mixed with DNA, iced for another 5 minutes, transferred to liquid nitrogen for 5 minutes, then incubated for 5 minutes in a 37° C. water bath. The cells are then grown and selected.

SUMMARY

In a first aspect, an illustrative embodiment provides an apparatus for genetically transforming cells. The apparatus includes but is not limited to a fluid that includes but is not limited to the cells and free genetic material, a container holding the fluid, an explosion chamber, an explosive material disposed in the explosion chamber, and an ignition system for igniting the explosive material in the explosion chamber to create a blast wave. The apparatus also includes but is not limited to a diaphragm having a propulsion surface acoustically coupled to the fluid, and a blast-receiving surface, opposite the propulsion surface, acoustically coupled to the explosion chamber such that the diaphragm is able to transfer pressure from the blast wave to the fluid sufficient to cause the cells to take up the free genetic material.

In other illustrative embodiments of the apparatus, the cells include but are not limited to bacterial cells.

In another illustrative embodiment, the free genetic material include but are not limited to plasmid DNA.

In other illustrative embodiments of the apparatus, the explosion chamber includes but is not limited to a polymer tube.

In other illustrative embodiments of this apparatus, the polymer tube includes but it not limited to a first open end acoustically coupled to the blast-receiving surface of the diaphragm and a second open end electrically coupled to the ignition system.

In other illustrative embodiments, the polymer tube includes but is not limited to a first end in contact with said blast-receiving surface of the diaphragm.

In other illustrative embodiments of this apparatus, the ignition system includes but is not limited to at least one electrode for creating a spark in the polymer tube.

In other illustrative embodiments of this apparatus, the ignition system includes but is not limited to a power supply for supplying a first voltage, a step-up voltage converter for stepping up the first voltage to a second voltage, a capacitor, at least one electrode in the explosion chamber, a first switch for causing the capacitor to be charged by the second voltage, and a second switch for causing the capacitor to discharge through at least one electrode.

In other illustrative embodiments of this apparatus, the diaphragm includes but is not limited to a metal foil having a thickness between about 100 µm and about 200 µm.

In a second aspect, an illustrative embodiment provides a method for genetically transforming cells. The method includes but is not limited to filling a container with a fluid, the fluid including the cells and free genetic material, positioning a diaphragm such that a propulsion surface of the diaphragm contacts the fluid medium in the container, the diaphragm having a blast-receiving surface opposite the propulsion surface, and positioning a tube, the tube having a first open end and a second open end, such that the first open end is acoustically coupled to the blast-receiving surface of the diaphragm, the tube having an explosive material disposed therein. The method also includes but is not limited to igniting the explosive material in the tube to create blast wave, wherein the diaphragm transfers pressure from the blast wave to the fluid sufficient to cause the cells to take up the free genetic material.

In other illustrative embodiments, the cells include but are not limited to bacterial cells.

In other illustrative embodiments of this method, the free genetic material includes but is not limited to plasmid DNA.

In other illustrative embodiments of this method, igniting the explosive material in the tube to create a blast wave includes but is not limited to applying electrical energy from a power supply to the explosive material in the tube.

In another illustrative embodiment, the tube is electrically coupled to the power supply by inserting at least one electrode into the second open end.

In other illustrative embodiments of this method, applying electrical energy from a power supply to the explosive material in the tube includes but is not limited to stepping up a first voltage from the power supply to a second voltage, charging a capacitor with the second voltage, and discharging the capacitor to create a spark in the tube.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
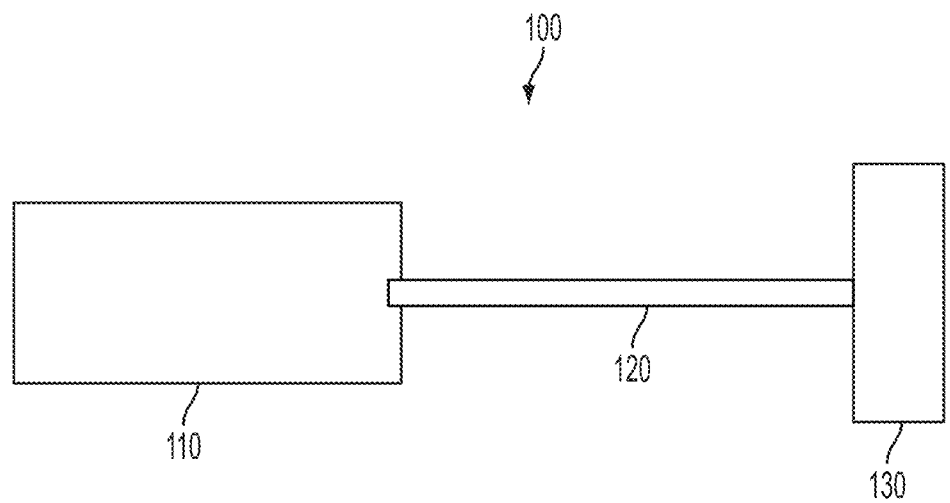
FIG. 1 is a schematic diagram of a cell transformation apparatus, in accordance with an illustrative embodiment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

1. Overview

To genetically transform cells an explosion chamber, explosive material, and an ignition system may be arranged to create a blast wave. The explosive material may be disposed in the explosion chamber and the ignition system may be used to ignite the explosive material and create the blast wave. The explosion chamber may comprise a polymer tube. The apparatus may include a diaphragm, which may have a propulsion surface acoustically coupled to a fluid that includes the cells and free genetic material and a blast-receiving surface opposite the propulsion surface. The blast-receiving surface may be acoustically coupled to the explosion chamber such that the diaphragm is able to transfer pressure from the blast wave to the fluid sufficient to cause the cells to take up the free genetic material. One example of a diaphragm may be a metal foil having a thickness between about 100 μm and about 200 μm.

The fluid including the cells and free genetic material may be held in a container. The cells may be bacterial cells and the free genetic material may comprise plasmid DNA.

The polymer tube may have a first open end acoustically coupled to the propulsion surface of the diaphragm and a second open end acoustically coupled to the ignition system. The first open end of the polymer tube may also be in contact with the propulsion surface of the diaphragm.

The ignition system may include at least one electrode for creating a spark in the polymer tube. The ignition system may include a power supply for supplying a first voltage, a step-up voltage converter for stepping up the first voltage to a second voltage, a capacitor, at least one electrode in the explosion chamber, a charging switch, and a firing switch. The charging switch may cause the capacitor to be charged by the second voltage when closed. The firing switch may cause the capacitor to discharge through at least one electrode when closed.

2. Handheld Device

FIG. 1 schematically illustrates a handheld device 100 that includes an ignition system 110, an explosion chamber 120, and a cell transformation apparatus 130. Device 100 may be used to transform cells, as described in more detail below.

Figure 2:
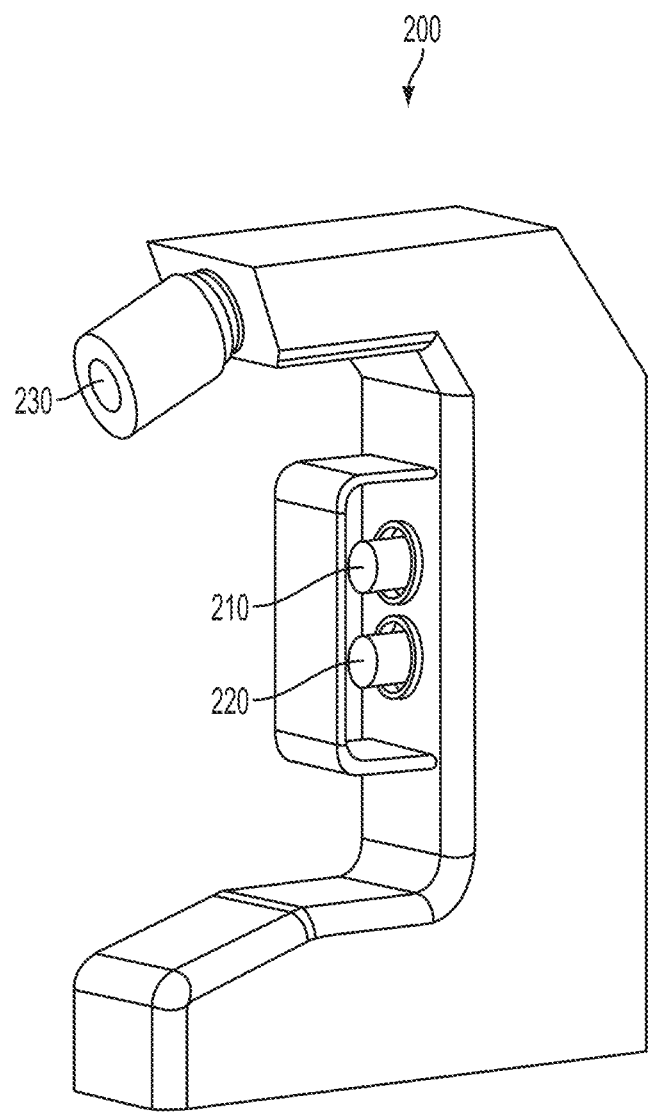
FIG. 2 is a perspective view of an ignition system, in accordance with an illustrative embodiment.

FIG. 2 is a perspective view of an illustrative ignition system 200 that may be used in device 100. Ignition system 200 may be dimensioned to be conveniently held by hand. Ignition system 200 includes a charging switch 210, a firing switch 220, and an electrode 230, with electrode 230 connected to explosion chamber 120. Ignition system 200 may be used to ignite explosive material in explosion chamber 120 and thereby create a blast wave that can be used to transform cells. In operation, the user may activate charging switch 210 to charge ignition system 200 and then activate firing switch 220 to ignite the explosive material. Ignition system 200 may be arranged in various configurations in addition to that illustrated in FIG. 2.

3. Apparatus for Genetically Transforming Cells

Figure 3:
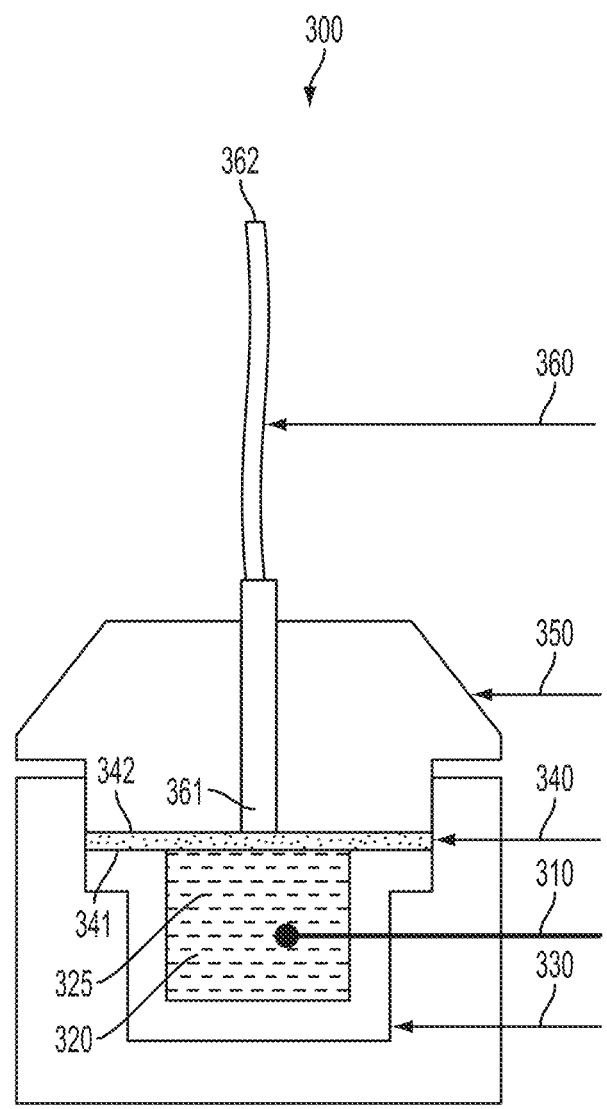
FIG. 3 is a schematic diagram of a cell transformation apparatus, in accordance with an illustrative embodiment.

FIG. 3 illustrates a cell transformation apparatus 300 that may be used to cause cells 310 to take up free genetic material 320. Cells 310 may be prokaryotic cells, such as bacterial cells. Free genetic material 320 may comprise plasmid DNA. Cells 310 and free genetic material 320 may be included in a fluid 325, which is held in a container 330. Container 330 may be cylindrical in shape. Container 330 may be made from a bio-inert material, such as MACOR® machinable-glass ceramic, or 316L stainless steel. The volume of container 330 may vary. For example, the volume may be 20 μL, 36 μL, or 57 μL, where the depth of the container is 3 mm and the diameter is varied.

Apparatus 300 may include a diaphragm 340 and a diaphragm holder 350. Diaphragm 340 has a propulsion surface 341 on one side and a blast-receiving surface 342 on an opposite side. Diaphragm 340 can be positioned such that propulsion surface 341 contacts fluid 325 in container 330. Diaphragm 340 may be a metal foil, such as aluminum, copper, brass, or silver. In illustrative embodiments, the thickness of diaphragm 340 is between about 100 μm and about 200 μm and the diameter of diaphragm 340 is about 12 mm. Diaphragm holder 350 may include multiple pieces connected together in order to hold diaphragm 340 firmly in place. Diaphragm holder 350 may be a metal casing.

Apparatus 300 also may include a tube 360 that functions as an explosion chamber. Tube 360 has a first open end 361 and a second open end 362, such that first open end 361 is acoustically coupled to blast-receiving surface 342 of diaphragm 340. In a representative embodiment, tube 360 may have a 1 mm inside diameter and a wall thickness of 1 mm. Tube 360 may be made from a variety of materials. For example, tube 360 may be a polymer. In a representative embodiment, tube 360 is a three-layer polymer, in which the inner layer is ionomer and the middle and outer layers are polyethylene. Tube 360 may also be made out of stainless steel.

Figure 4:
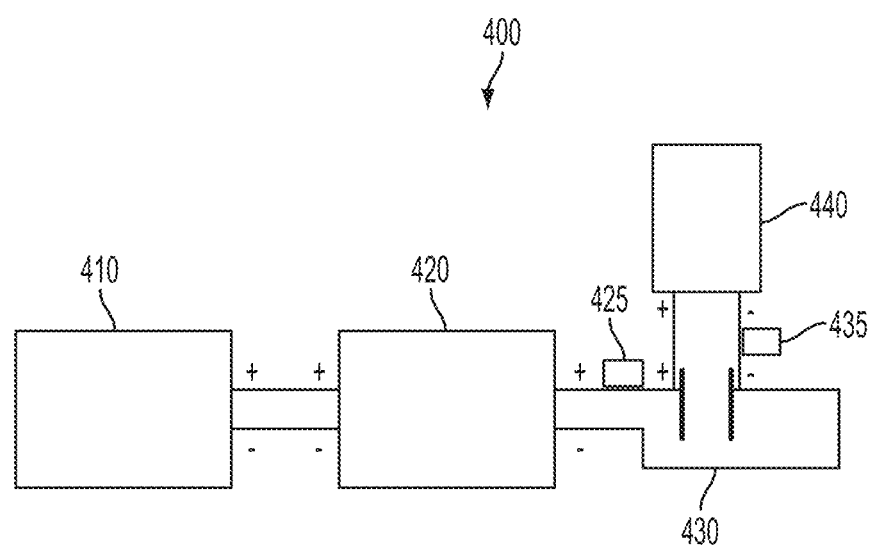
FIG. 4 is a schematic diagram of the ignition system of FIG. 2, in accordance with an illustrative embodiment.

Tube 360 may contain explosive material, which can be ignited to create a blast wave. The explosive material may be coated on the inner wall of tube 360. In an example embodiment, the explosive material is a mixture of HMX and aluminum with a particle size of 20 microns, wherein the aluminum is applied at 2 mg/m length and the HMX is applied at 16 mg/m length. The explosive material may be ignited by applying electrical energy from an ignition system, such as shown in FIG. 4. Tube 360 may also be electrically coupled to the ignition system by inserting at least one electrode into second open end 362. Diaphragm 340 then transfers pressure from the blast wave to fluid 325 sufficient to cause cells 310 to take up free genetic material 320.

FIG. 4 illustrates an ignition system 400 that may be used to ignite the explosive material. Ignition system 400 may include a power supply 410, a step-up voltage converter 420, a capacitor 430, and at least one electrode 440. In illustrative embodiments, there is a spark gap in the electrodes, which may be in the range of about 0.5 mm to about 1 mm. Ignition system 400 may also include a charging switch 425, located between voltage convertor 420 and capacitor 430, and a firing switch 435, located between capacitor 430 and electrode 440. In a representative embodiment, power supply 410 supplies a first voltage, step-up voltage converter 420 steps up the first voltage to a second voltage, capacitor 430 is charged with the second voltage, and capacitor 430 is discharged to create a spark in tube 360.

In an illustrative embodiment, power supply 410 is a 9V alkaline battery and capacitor 430 is a 0.2 µF capacitor. Voltage converter 420 converts the 9V to 2500V. When the user activates charging switch 425, capacitor 430 is charged up to 2500V. When the user activates firing switch 435, capacitor 430 discharges through electrode 440 to create a spark. The spark ignites the explosive material to create a blast wave. The blast wave travels the length of tube 360. In an illustrative embodiment, the blast wave travels at a rate of about 2000 m/s. The blast wave deforms diaphragm 340. During the process of deformation, diaphragm 340 transfers the pressure from the blast wave to fluid 325 such that cells 310 take up free genetic material 320.

In illustrative embodiments, $Escherichia\ coli$ (DH5-α) competent cells can be used. To prepare such cells, fresh overnight-grown cultures of $E.\ coli$ (DH5-α) can be inoculated to 100 ml LB and allowed to grow at 37° C. for 3-4 hours until $OD_{600}$ reaches 0.4-0.5. The culture is then cooled in ice for 15 minutes and centrifuged at 3000 rpm for 7 minutes at 4° C. The pellet is then dissolved in 10 ml of transformation-storage buffer (TSB, PEG4000-10%, DMSO 5%, $MgCl_2$ 10 mM, $MgSO_4$ 10 mM, Glycerol 10 v/v, LB 6.1 pH) and centrifuged for 7 minutes at 4° C. The resulting pellet is then resuspended in 5 ml of TSB. The resuspended cells are frozen in liquid nitrogen and stored in 100 µl aliquots at −70° C.

In illustrative embodiments, prokaryotic cells, such as the ones described above, are mixed with cloning vector type naked plasmid DNA in a cavity and are covered with a metal diaphragm. The metal diaphragm is exposed to a blast wave emanating from the end of the polymer tube. The metal diaphragm deforms instantaneously and transmits the blast wave through the bacterial cell suspension, inducing the prokaryotic cells to take up the plasmid DNA. The cell transformation is confirmed by the growth of cells in plates containing antibiotic Kanamycin. The isolated colonies are counted to express the transformation efficiency. Transformation experiments have been carried out with $E.\ coli$ and $Agarobacterium\ tumifaciens$ cells with plasmid DNA.

In representative embodiments, the plasmid used may be pTZ57R/T (Size–2.8 kb)+ELIP gene–T/A vector or pCAMBIA1302 (Size–8.2 kb)+GUS (Size 1.8 kb)–Total Plasmid size–10 kb, which after transformation contain the gene that is resistant to Kanamycin.

Figure 5:
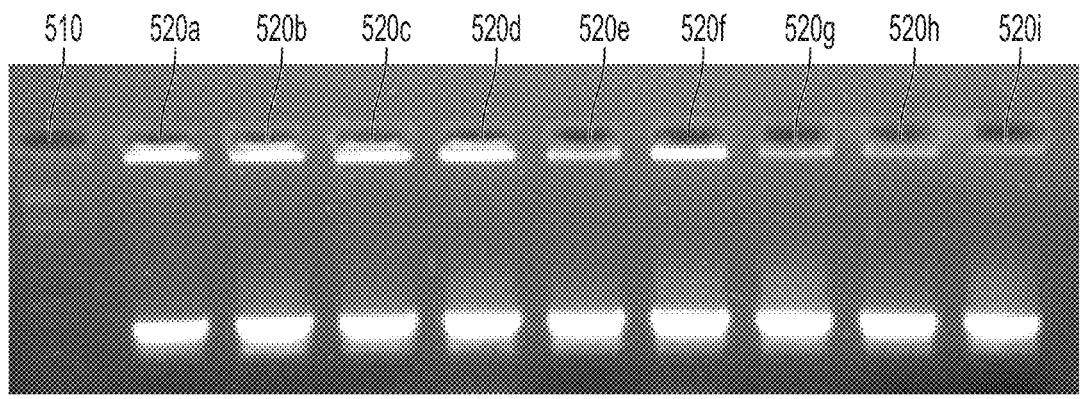
FIG. 5 is a digital image of colony polymerase chain reaction results of a blast wave assisted cell transformation of *E. coli* (DH5-α).

FIG. 5 shows the results obtained from polymerase chain reactions (PCR) in a blast wave experiment with $E.\ coli$ (DH5-α). In FIG. 5, lane 510 represents a DNA ladder and lanes 520a-i represent $E.\ coli$ colonies that have grown in an anti-biotic medium. In addition, successful gene transformation in $Agarobacterium$ has been confirmed by tracking reporter DNA in tomato plants.

Figure 6:
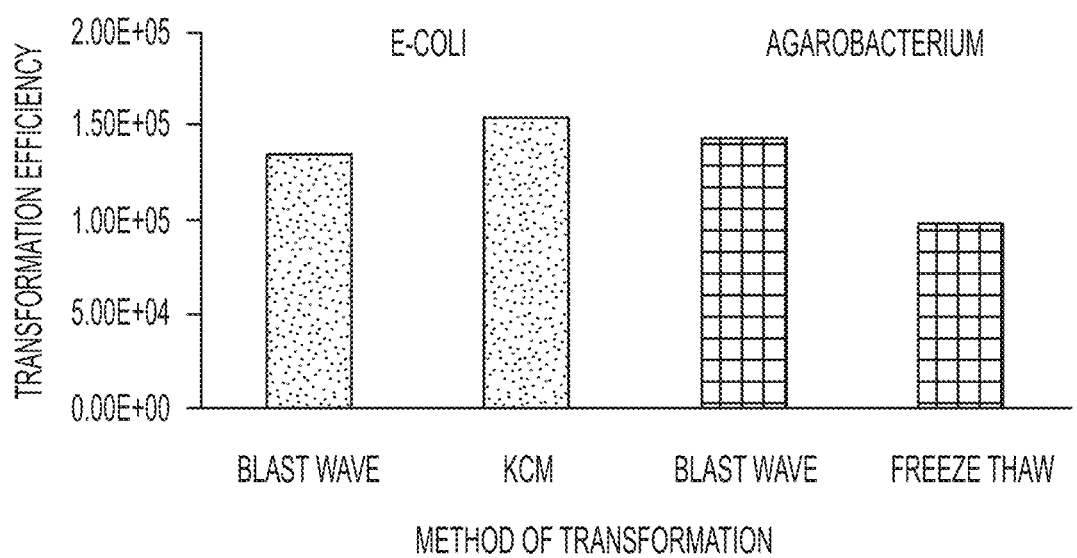
FIG. 6 is a graph of transformation efficiencies in relation to the method of transformation.

FIG. 6 compares the transformation efficiencies of $E.\ coli$ and $Agarobacterium$ using different methods of transformation, such as blast wave, KCM, and freeze thaw. In illustrative embodiments, effective transformation has been observed for $E.\ coli$ at a 50 bar pressure pulse for 5 microseconds.

Illustrative embodiments of the cell transformation apparatus have been described above. It is to be understood, however, that a cell transformation apparatus could be constructed and/or used in other ways.

4. Illustrative Applications

By using apparatuses as shown and described here, cells can be transformed with free genetic material without any contamination. Using these apparatuses and the desired DNA, mRNA can be introduced into the cell without destroying the biological entity. Because these devices may be handheld devices, they can be easy to use and transport. These devices can be used where conventional electroporators are used, such as in biotechnology industries and laboratories. Because these devices do not allow the biological fluid to come into contact with any other fluid, the need for consumables is minimized. In addition, these devices can be manufactured indigenously and for a low cost.

5. Conclusion

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions, or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method for genetically transforming cells, comprising:
   filling a container with a fluid, said fluid including said cells and free genetic material;
   positioning a diaphragm such that a propulsion surface of said diaphragm contacts said fluid medium in said container, said diaphragm having a blast-receiving surface opposite said propulsion surface;
   positioning a tube, said tube having a first open end and a second open end, such that said first open end is acoustically coupled to said blast-receiving surface of said diaphragm, said tube having an explosive material disposed therein; and
   igniting said explosive material in said tube to create blast wave with a peak pressure that does not exceed 5 MPa, wherein said diaphragm transfers pressure from said blast wave to said fluid sufficient to cause said cells to take up said free genetic material.

2. The method of claim 1, wherein said cells are bacterial cells.

3. The method of claim 2, wherein said free genetic material comprises plasmid DNA.

4. The method of claim 1, wherein igniting said explosive material in said tube to create a blast wave comprises:
   applying electrical energy from a power supply to said explosive material in said tube.

5. The method of claim 4, further comprising: electrically coupling said tube to said power supply by inserting at least one electrode into said second open end.

6. The method of claim 4, wherein applying electrical energy from a power supply to said explosive material in said tube comprises:
   stepping up a first voltage from said power supply to a second voltage;
   charging a capacitor with said second voltage; and
   discharging said capacitor to create a spark in said tube.

7. The method of claim 1, wherein said explosive material comprises conventional HMX.

8. The method of claim 7, wherein said explosive material is a mixture of conventional HMX with aluminium powder.

9. The method of claim 1, wherein said explosive is coated at about 18 mg/m on the interior surface of said tube.

\* \* \* \* \*

UNITED STATES PATENT AND TRADEMARK OFFICE
CERTIFICATE OF CORRECTION

PATENT NO. : 8,513,019 B2  
APPLICATION NO. : 13/560086  
DATED : August 20, 2013  
INVENTOR(S) : Jagadeesh Page 1 of 1

It is certified that error appears in the above-identified patent and that said Letters Patent is hereby corrected as shown below:

In the Specification

In Column 5, Lines 49-50, delete "Agarobacterium tumifaciens" and insert -- Agrobacterium tumefaciens --, therefor.

In Column 5, Line 61, delete "Agarobacterium" and insert -- Agrobacterium --, therefor.

In Column 5, Line 64, delete "Agarobacterium" and insert -- Agrobacterium --, therefor.

Signed and Sealed this  
Twelfth Day of November, 2013

Teresa Stanek Rea  
*Deputy Director of the United States Patent and Trademark Office*